(12) United States Patent
Hu et al.

(10) Patent No.: US 11,131,662 B2
(45) Date of Patent: Sep. 28, 2021

(54) DETECTION DEVICE FOR DETECTING ANALYTES IN LIQUID SPECIMEN

(71) Applicant: Abon Biopharm (Hangzhou) Co., Ltd, Zhejiang (CN)

(72) Inventors: Lin Hu, Hangzhou (CN); Haipeng Hu, Lin'an (CN); Yinfei Wu, Hangzhou (CN)

(73) Assignee: Abon Biopharm (Hangzhou) Co., Ltd., Zhejiang (CN)

( * ) Notice: Subject to any disclaimer, the term of this patent is extended or adjusted under 35 U.S.C. 154(b) by 139 days.

(21) Appl. No.: 16/126,679

(22) Filed: Sep. 10, 2018

(65) Prior Publication Data

US 2018/0372729 A1    Dec. 27, 2018

Related U.S. Application Data

(62) Division of application No. 13/636,326, filed as application No. PCT/CN2011/072179 on Mar. 25, 2011, now Pat. No. 10,073,088.

(30) Foreign Application Priority Data

Mar. 25, 2010    (CN) ............................. 201010155071

(51) Int. Cl.
*G01N 33/53* (2006.01)
*B01L 3/00* (2006.01)

(52) U.S. Cl.
CPC .......... *G01N 33/5302* (2013.01); *B01L 3/502* (2013.01); *B01L 3/508* (2013.01); *B01L 2300/042* (2013.01); *B01L 2400/0655* (2013.01); *Y10T 436/141111* (2015.01); *Y10T 436/142222* (2015.01); *Y10T 436/145555* (2015.01); *Y10T 436/146666* (2015.01); *Y10T 436/147777* (2015.01); *Y10T 436/173076* (2015.01); *Y10T 436/173845* (2015.01)

(58) Field of Classification Search
None
See application file for complete search history.

(56) References Cited

U.S. PATENT DOCUMENTS

| | | | |
|---|---|---|---|
| 4,349,035 A | 9/1982 | Thomas et al. |
| 5,252,496 A | 10/1993 | Kang et al. |
| 5,415,994 A | 5/1995 | Imrich et al. |
| 5,559,041 A | 9/1996 | Kang et al. |
| 5,602,040 A | 2/1997 | May et al. |
| 5,656,503 A | 8/1997 | May et al. |
| 5,712,170 A | 1/1998 | Kouvonen et al. |
| 5,877,028 A | 3/1999 | Chandler et al. |
| 5,922,283 A | 7/1999 | Hsu |
| 5,965,458 A | 10/1999 | Kouvonen et al. |
| 6,046,058 A | 4/2000 | Sun |
| 6,136,610 A | 10/2000 | Polito et al. |
| 6,140,136 A | 10/2000 | Lee |
| 6,183,972 B1 | 2/2001 | Kuo et al. |
| 6,187,268 B1 | 2/2001 | Albarella et al. |
| 6,187,598 B1 | 2/2001 | May et al. |
| 6,194,221 B1 | 2/2001 | Rehg et al. |
| 6,194,224 B1 | 2/2001 | Good et al. |
| 6,221,678 B1 | 4/2001 | Chandler |
| 6,228,660 B1 | 5/2001 | May et al. |
| 6,241,689 B1 | 6/2001 | Chard et al. |
| 6,248,598 B1 | 6/2001 | Bogema |
| 6,271,046 B1 | 8/2001 | Chandler |
| 6,297,020 B1 | 10/2001 | Brock |
| 6,316,205 B1 | 11/2001 | Guan et al. |
| 6,338,969 B1 | 1/2002 | Shareef et al. |
| 6,368,873 B1 | 4/2002 | Chang et al. |
| 6,372,514 B1 | 4/2002 | Lee |
| 6,372,516 B1 | 4/2002 | Sun |
| 6,375,896 B1 | 4/2002 | Wuske et al. |
| 6,375,897 B1 | 4/2002 | Bachand |
| 6,391,652 B2 | 5/2002 | Okada et al. |
| 6,403,383 B1 | 6/2002 | Casterlin et al. |
| 6,418,606 B1 | 7/2002 | Bachand |
| 6,429,026 B1 | 8/2002 | Pettersson et al. |
| 6,440,369 B1 | 8/2002 | Oonuma et al. |
| 6,464,939 B1 | 10/2002 | Bachand et al. |

(Continued)

FOREIGN PATENT DOCUMENTS

| | | |
|---|---|---|
| CN | 1495420 A | 5/2004 |
| CN | 2724003 Y | 9/2005 |

(Continued)

OTHER PUBLICATIONS

Office Action received for European Patent Application No. 11758816, dated Dec. 6, 2017, 4 pages.
International Search Report and Written Opinion received for PCT Patent Application No. PCT/CN2011/072179, dated Jul. 7, 2011, 14 pages.
International Preliminary Report on Patentability received for PCT Patent Application No. PCT/CN2011/072179, dated Oct. 4, 2012, 9 pages.

(Continued)

*Primary Examiner* — Andrea S Grossman
(74) *Attorney, Agent, or Firm* — Edward J. Baba; Mandar A. Joshi; Bozicevic, Field & Francis LLP

(57) ABSTRACT

A detection device for detecting analytes in liquid specimen is provided. The detection device comprises: a specimen chamber for collecting or storing a liquid specimen; a detecting chamber for containing a detecting element; and a through hole for transferring the liquid specimen between the specimen chamber and the detecting chamber. The through hole can be opened or self-sealed. The sealing or opening of the through hole controls whether or not the liquid specimen in the specimen chamber enters the detecting chamber via the through hole. Furthermore, a detection method is provided.

3 Claims, 11 Drawing Sheets

(56) References Cited

U.S. PATENT DOCUMENTS

| | | |
|---|---|---|
| 6,468,474 B2 | 10/2002 | Bachand et al. |
| 6,485,982 B1 | 11/2002 | Charlton |
| 6,506,612 B2 | 1/2003 | Kang et al. |
| 6,514,768 B1 | 2/2003 | Guire et al. |
| 6,514,769 B2 | 2/2003 | Lee |
| 6,528,323 B1 | 3/2003 | Thayer et al. |
| 6,537,823 B1 | 3/2003 | Smith |
| 6,548,019 B1 | 4/2003 | Lee et al. |
| 6,730,268 B2 | 5/2004 | Lee et al. |
| 7,300,633 B2 | 11/2007 | Hudak et al. |
| 8,323,583 B2 | 12/2012 | Gou et al. |
| 2001/0004532 A1 | 6/2001 | Chandler |
| 2001/0021536 A1 | 9/2001 | Lee |
| 2001/0023076 A1 | 9/2001 | Guan et al. |
| 2002/0001845 A1 | 1/2002 | Klaemer et al. |
| 2002/0001854 A1 | 1/2002 | Lee |
| 2002/0004019 A1 | 1/2002 | Bachand et al. |
| 2002/0031840 A1 | 3/2002 | Albarella et al. |
| 2002/0031845 A1 | 3/2002 | Cipkowski |
| 2002/0052050 A1 | 5/2002 | Douglas et al. |
| 2002/0085953 A1 | 7/2002 | Parker |
| 2002/0098512 A1 | 7/2002 | Goodell et al. |
| 2002/0132267 A1 | 9/2002 | Wong |
| 2002/0137231 A1 | 9/2002 | Cipkowski |
| 2002/0155028 A1 | 10/2002 | Wong |
| 2002/0173047 A1 | 11/2002 | Hudak et al. |
| 2003/0027359 A1 | 2/2003 | Hudak et al. |
| 2003/0045003 A1 | 3/2003 | Smith |
| 2003/0099572 A1 | 5/2003 | Ng et al. |
| 2003/0129673 A1 | 7/2003 | Schwarz et al. |
| 2003/0207466 A1 | 11/2003 | Lee |
| 2004/0018636 A1 | 1/2004 | Zhou et al. |
| 2004/0060374 A1 | 4/2004 | Goodin |
| 2004/0191760 A1 | 9/2004 | Zhou et al. |
| 2005/0048670 A1 | 3/2005 | Wu et al. |
| 2005/0106750 A1 | 5/2005 | Tung et al. |
| 2006/0029517 A1 | 2/2006 | Hartselle |
| 2006/0224129 A1 | 10/2006 | Beasley et al. |
| 2007/0092402 A1 | 4/2007 | Wu et al. |
| 2007/0134134 A1 | 6/2007 | Watts et al. |
| 2007/0140915 A1* | 6/2007 | Sakai .................... B01L 3/0272 422/400 |
| 2009/0019953 A1 | 1/2009 | Bommarito et al. |
| 2009/0031790 A1* | 2/2009 | Guo .................... A61B 10/007 73/64.56 |
| 2009/0143249 A1 | 6/2009 | Besemer et al. |
| 2009/0308185 A1 | 12/2009 | Wu et al. |
| 2013/0045501 A1 | 1/2013 | Hu et al. |

FOREIGN PATENT DOCUMENTS

| | | |
|---|---|---|
| CN | 1774629 A | 5/2006 |
| CN | 1834622 A | 9/2006 |
| CN | 1842299 A | 10/2006 |
| CN | 1882831 A | 12/2006 |
| CN | 201159737 Y | 12/2008 |
| CN | 101498655 A | 8/2009 |
| CN | 201583537 U | 9/2010 |
| CN | 201666896 U | 12/2010 |
| EP | 0289761 A2 | 11/1988 |
| WO | 95/21382 A2 | 8/1995 |
| WO | 2004074829 A1 | 9/2004 |
| WO | 2005/119253 A1 | 12/2005 |
| WO | 2007/070740 A2 | 6/2007 |
| WO | 2008/042033 A2 | 4/2008 |

OTHER PUBLICATIONS

European Search Report and Search Opinion Received for EP Application No. 1175881, dated Oct. 30, 2013, 5 pages.

* cited by examiner

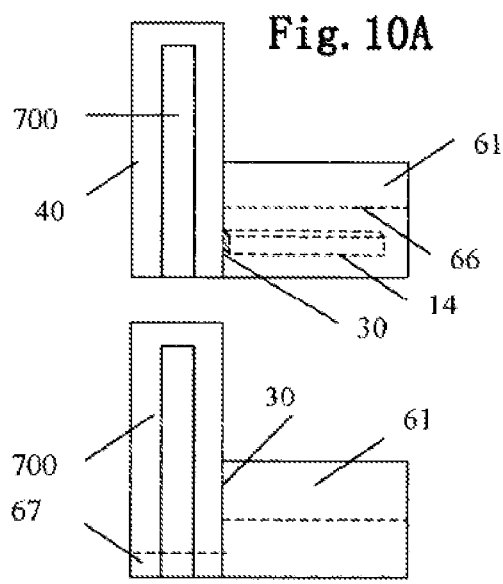
Fig. 10A
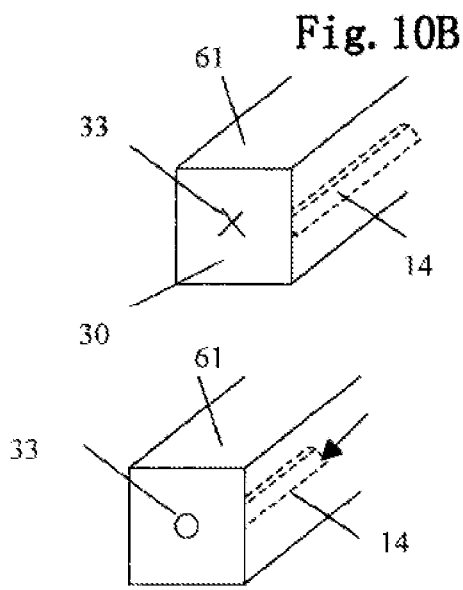
Fig. 10B
Fig. 10C
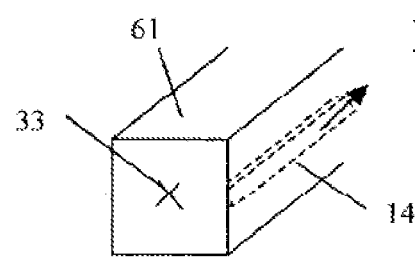
Fig. 10D
Fig. 10E
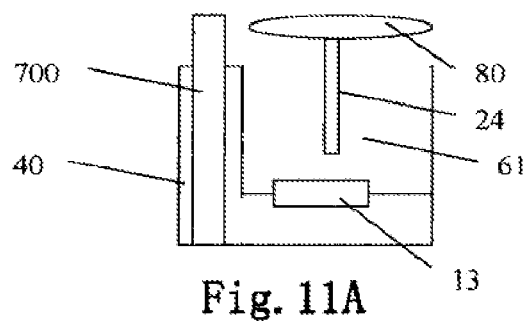
Fig. 11A
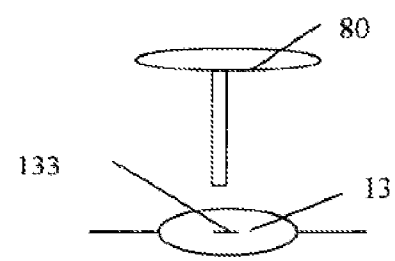
Fig. 11B
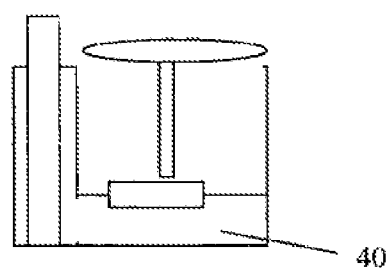
Fig. 11C
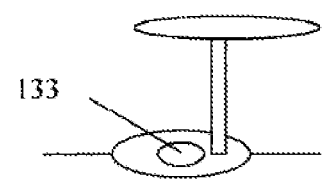
Fig. 11D

DETECTION DEVICE FOR DETECTING ANALYTES IN LIQUID SPECIMEN

CROSS-REFERENCE TO RELATED APPLICATIONS

This application is a divisional application of U.S. Ser. No. 13/636,326 filed Nov. 1, 2012, now issued as U.S. Pat. No. 10,073,088; which is a 35 USC § 371 National Stage application of International Application No. PCT/CN2011/072179 filed Mar. 25, 2011, now expired; which claims the benefit under 35 USC § 119(a) to China Patent Application No. 201010155071.0 filed Mar. 25, 2010, now expired. The disclosure of each of the prior applications is considered part of and is incorporated by reference in the disclosure of this application.

BACKGROUND OF THE INVENTION

Field of the Invention

The present invention is in the field of collecting liquid specimen, in particular the field of collecting liquid specimen and detecting analytes in the specimen, especially for detecting whether the specimen contains metabolites of abused drugs or for quick diagnosis and detection of pregnancy.

Background Information

In recent years, detection devices are widely used for detecting analytes such as substances indicating drug-abuse or diseases in human fluids such as urine, saliva or blood. In this way, the traditional detection devices generally need to collect liquid specimen into a container, then a detecting element is inserted into the liquid and is taken out to have the detecting results on the detecting element read (with eyes or machines). Therefore, it is possible that the operator may be contaminated by the specimen. Besides professionals, these detection devices are also widely used by ordinary people without professional experiences, such as used in daily life by family members. Therefore, there are demands to provide detection devices that can be operated more easily yet provide even more accurate detecting results.

SUMMARY OF THE INVENTION

To overcome defects of the present devices, the present invention provides a device for rapid detection, which can be easily operated and is acceptable to ordinary people.

One aspect of the invention relates to a detection device, comprising a chamber for collecting or storing liquid specimen, and a detecting chamber, and a through hole that can be opened or self-sealed. The passing of the liquid specimen between the specimen chamber and the detecting chamber can be controlled by self-sealing or opening of the through hole. When the through hole is opened, the liquid in the specimen chamber and the detecting chamber is in liquid communication via the through hole, and part of the liquid specimen can flow into the detecting chamber via the through hole and have contact with the detecting element. Otherwise, when the opened through hole is self-closed or self-sealed, the specimen chamber cannot be in liquid communication with the detecting chamber via the through hole, and the liquid specimen cannot flow into the detecting chamber via the through hole. In one optional embodiment, the through hole is in its first status when the through hole is self-closed or sealed, and it is in the second status when the through hole is opened from the self-closed status and is in an open status. The first status can be that the through hole is in natural status and is free of external force or the external force is not sufficient to open the self-sealed or closed through hole; the second status can be that the through hole is forced to be opened by the external force. In another optional embodiment, when the external force that acts on the through hole in the second status disappears, the through hole can go back to the first status, i.e., the through hole goes back to the self-closed or self-sealed status from the open status.

The through hole having the above one or more functions can be self-sealed or opened under certain conditions, due to the fact that the through hole is made from certain materials. For example, the through hole can be made on a flexible material, as a small slot that is cut on the flexible material by a knife. Without any external force, the small slot would be in sealed or closed status due to the self-shrinking ability because of the inherent property of the material. In this case the liquid specimen in the specimen chamber could not get into the detecting chamber through the small slot. However, when the shape of the flexible material changes due to, for example, actions of external force, or the property of the material changes when, for example, the outside environment changes, the small slot is opened and the liquid specimen in the specimen chamber could get into the detecting chamber via the small slot, thus accomplishing the detecting test.

In some embodiments, the through hole can be located on a flexible element. When the flexible element is in the first status, the through hole is self-sealed or self-closed because of the inherent flexibility of the material. When the flexible element is in the second status, the through hole is in its second status and opened, a channel is thus formed between the specimen chamber and the detecting chamber, whereby the liquid specimen in the specimen chamber can enter into the detecting chamber via the through hole, thus accomplishing the detecting test. In a more specific embodiment, the first status of the flexible element is its natural status; when the flexible element is forced to be in the second status, its shape changes due to the external force. When the flexible element is in the natural status, the small slot on the flexible element that is cut in advance, which is the through hole, shrinks naturally and is in the sealed status. When the flexible element undergoes a shape change due to an external force, the shrunk small slot is opened, thus forming a channel between the specimen chamber and the detecting chamber, and the liquid specimen in the specimen chamber can flow into the detecting chamber through the open small slot. In some embodiments, the flexible element can have a third status. When the flexible element is in the third status, the opened through hole also goes back to be self-sealed or self-closed, thus the liquid in the specimen chamber cannot get into the detecting chamber via the through hole. This sealing or closing of the through hole when the flexible element is in the third status can be achieved by the inherent property of the flexible elements, i.e., the external force on the flexible element disappears or is reduced to a certain degree so that the opened through hole can close or seal itself due to its inherent rebound force, or it can be achieved by other means including external forces.

The flexible element can be made from flexible materials including plastics, rubber or silica gel. Rubber includes, but is not limited to, one or more types of natural rubber, styrene-butadiene rubber, cis-butadiene rubber, chloroprene rubber, nitrile butadiene rubber, butyl rubber, ethylenepropylene rubber, fluororubber, polyurethane rubber, polysulfide rubber, epichlorohydrin rubber or latex. The flexible element can also be made of other materials and have the ability of accomplishing the following functions, i.e., opening a through hole or a small slot on the flexible material, and the small slot is self-shrunk to form a sealed or closed status when in the first status and thus the liquid specimen in the specimen chamber cannot get into the detecting chamber via the shrunk through hole; the through hole is opened when in the second status and thus the liquid specimen in the specimen chamber can get into the detecting chamber via the opened small slot. The through hole that is self-sealed or closed can be opened through changing status of the through hole by applying the external force on the through hole or other positions of the flexible element, where the hole is located. The external force can be applied directly or indirectly.

In some other embodiments, the flexible element is "nipple shaped", the through hole is located on the side wall of the nipple. When in the first status of the natural status, the teat is towards right, and the through hole is in the sealed status due to the inherent property of the material composing the nipple or the shape itself. In this case, the liquid inside the specimen chamber cannot get into the detecting chamber via the through hole on the nipple. The nipple is in the second status when it is turned over or is forced towards left by external forces. The interior surface of the nipple is turned into the exterior surface at this time, and the through hole that is in self-sealed status is opened because the shape of the nipple is changed, thus the liquid in the specimen chamber can get into the detecting chamber via the through hole on the nipple. Of course, the nipple can be returned to the first status from the second status, or goes into a third status, and then the through hole on the nipple is changed to the self-sealed status from the open status.

In some embodiments, the device can further comprise a rod, and whether the through hole is sealed or opened can be controlled by controlling the movement of the rod, whereby whether the liquid specimen in the specimen chamber can flow into the detecting chamber via the through hole is controlled. For example, when the rod is at a first position, the through hole remains sealed, the liquid specimen in the specimen chamber cannot get into the detecting chamber via the through hole to have contact with the detecting element; when the rod moves from the first position to a second position, the through hole that is in the sealed status is opened due to position change of the rod, whereby the liquid specimen in the specimen chamber gets into the detecting chamber via the opened through hole to have contact with the detecting element. In a more specific embodiment, the through hole can be located on a flexible element, when the rod is at the first position, the through hole on the flexible element is shrunk naturally to form a sealed through hole due to its inherent flexibility; when the rod moves to a second position from a first position, the rod makes the flexible element undergo elastic deformation, and the originally naturally sealed through hole is opened, whereby the liquid flowing between the specimen chamber and the detecting chamber is under control.

In some other embodiments, the rod is connected with a piston, and the position of the rod is changed by changing the position of the piston. The position of the rod can be changed from top to bottom or from bottom to top, or from right to left or from left to right. The position of the piston can be changed from top to bottom or from bottom to top, or from right to left or from left to right.

In some other embodiments, the detection device can further include a liquid transferring chamber, and the liquid specimen in the specimen chamber flows into the detecting chamber via the transferring chamber, and a through hole that can be self-sealed or opened is located on the transferring chamber to control the passing of the liquid. The through hole is sealed when in the first status because of the inherent property of the material, whereby the liquid specimen in the specimen chamber cannot get into the detecting chamber via the through hole; when the through hole is in the second status, the sealed through hole is opened, and the liquid specimen in the specimen chamber can get into the detecting chamber via the through hole. In some other embodiments, the through hole is self-sealed when in the first status, and the liquid transferring chamber is in communication with the specimen chamber, and the through hole is opened when in the second status, and the liquid transferring chamber is not in communication with the liquid specimen chamber, and the liquid in the liquid transferring chamber is in communication with the detecting chamber via the opened through hole. In more specific embodiments, the piston can be inside the liquid transferring chamber, and the status of the flexible element is changed by changing the position of the piston, thereby changing the status of the through hole.

In some other embodiments, the device can further include a lid covered on the specimen chamber, and in the process that the lid covers the specimen chamber, the through hole that is self-sealed is opened through moving a rod that is connected to the lid.

The detecting chamber is a space or a compartment wherein the detecting element is contained. In an embodiment, the detecting chamber can be on the lid. And in other embodiments, the detecting chamber can be physically separated from the lid, but it has the same function as the one on the lid. For example, in some embodiments, the detecting chamber can be inside or outside the specimen chamber. "Transparency" denotes a type of material that the light can pass through so that the subject behind the transparent material can be seen by humans' naked eyes in normal room light, and a person using the device can see the detecting results under the transparent window. A "cup" denotes not only conventional substantially round or elliptic containers, but also those with any optional shapes. Therefore, a cup can also be square or a shape suitable for fulfilling the function of a cup. Moreover, the lid can comprise a helicitic texture described in the present invention, or a latch structure latched to the top of the cup, or a cork that can be squeezed into the cup container and fixed therein by the cork's swelling pressure. When the helicitic texture is used, the depth of the thread is not limited, and it can have several circles, one circle, or even less than one circle thread, as far as the lid is fixed on the cup. In some embodiments, the cup and the lid are all round.

Another aspect of the present invention provides a method for detecting analytes in specimen, comprising:
   a) providing a device, which comprises a detecting chamber for containing a detecting element, a collecting chamber for collecting liquid specimen, and a through hole that can be self-sealed or opened;
   b) opening the through hole and allowing part of the liquid specimen to flow into the detecting chamber from the collecting chamber via the through hole, or allowing the through hole to be self-sealed so that the collecting chamber is not in liquid communication with the detecting chamber.

Optionally, the method further comprises: the through hole is on a flexible element; when the flexible element is in a first status, the through hole is self-sealed; and when the flexible element is in a second status, the through hole is opened. The method can further comprise: a rod is applied on the through hole, when the rod is pushed to move from the first position to the second position, the through hole is accordingly changed to the second status from the first status. Optionally, a rod is applied directly on the flexible element, and when the rod is pushed to move from the first position to the second position, the flexible element changes from the first status to the second status.

Also optionally, the method further comprises that, after the through hole is opened, allowing the through hole to change from the second status back to the first status, so that the through hole is self-sealed again, and the collecting chamber is not in liquid communication with the detecting chamber any more.

The device provided by the present invention makes the operation of the detection device simpler and more straightforward, which is different from the conventional detection devices.

BRIEF DESCRIPTION OF THE DRAWINGS

FIG. 10A is a sectional schematic diagram of the structure of the detection device in a specific example of the present invention, wherein the flexible element is in the first status and the through hole is self-sealed or closed; FIG. 10B is a stereostructural schematic diagram when the flexible element is in the first status; FIG. 10D is a stereostructural schematic diagram when the flexible element is in the second status and the through hole is opened; FIG. 10C is a sectional schematic diagram of the structure of the device shown in FIG. 10A, wherein the flexible element is in the second status and the through hole is opened; FIG. 10E is a stereostructural schematic diagram when the flexible element is in the third status, wherein the flexible element goes back to be self-sealed or closed, as it is in the first status.

FIG. 11A is a sectional schematic diagram of the structure of the detection device in a specific example of the present invention, wherein the flexible element is in the first status and the through hole is self-sealed or closed; FIG. 11B is a stereostructural schematic diagram wherein the flexible element is in the first status; FIG. 11C is a sectional schematic diagram of the structure of the device shown in FIG. 11A, wherein the flexible element is in the second status and the through hole is opened; FIG. 11D is a stereostructural schematic diagram wherein the flexible element is in the second status and the through hole is opened.

DESCRIPTION OF REFERENCE INDEXES

Figure 1:
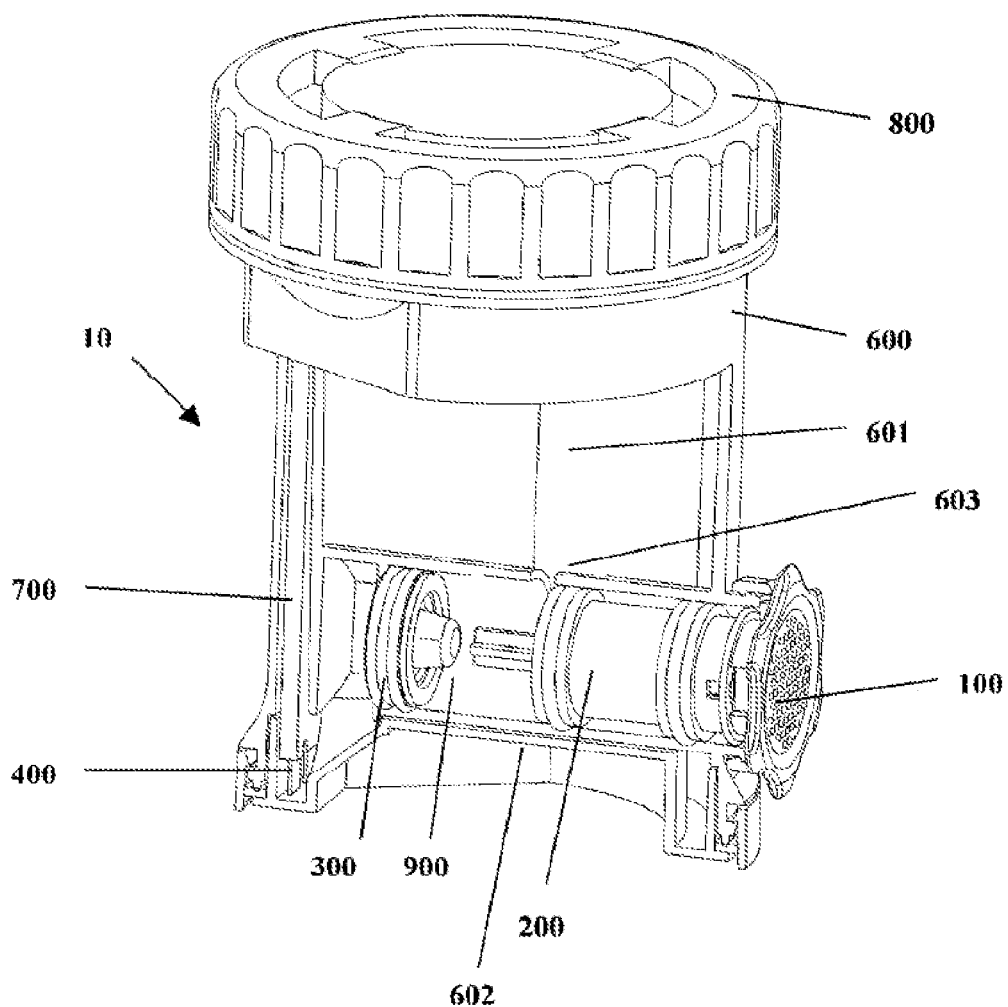
FIG. 1 is a stereostructural schematic diagram of the detection device described in a specific example of the present invention.

Detection device 10; detecting element 700; cover 800, 80; detecting chamber 400, 40; flexible element 30, 13; cutting slot 33; small hole 133; cup body 600; collecting chamber 601, 61; seat base 602 of the cup body, opening 606 of the cup body; transferring chamber 500; opening 501 at one end of the transferring chamber, opening 502 at the other end of the transferring chamber; annular convex edge 503 at the base of the transferring chamber; channel 603; nipple element 300; nipple seat base 301; side wall 304 of nipple; nipple cutting slot 303; nipple chamber 305; nipple top 304; rod 204, 24, 14; rod top 205; nipple groove 306; piston 200; outside wall 203 of piston; a first sealing ring 201; a second sealing ring 202; a first clamp strip 207, end 208 of the first clamp strip; a second clamp strip 206; end 209 of the second clamp strip, first pair of clamp slots 105, 105'; second pair of clamp slots 104, 104'; piston push rod 100; push rod head 101; piston push rod body 103; outside wall 108 of the push rod body; chamber 210 of the piston 200.

DETAILED DESCRIPTION OF THE INVENTION

In the following detailed description, the figures and the corresponding description are used to explain the particular specific embodiments of the present invention. These specific embodiments are just used as examples for illustrating the invention. Skilled artisans understand that any other specific embodiments that comply with the scope of the claims in the present invention should also be included in the present invention.

On one hand, the present invention provides a detection device for detecting analytes in liquid specimen. The device can detect and test the liquid specimen without contaminating the remaining liquid specimen. Further, the detecting is completed in one step without involving complicated operational steps.

Referring to FIG. 10, a detection device of the present invention comprises a specimen chamber 61 for collecting or storing liquid specimen; and a detecting chamber 40 comprising a detecting element 700; the detecting element can be a lateral flow immunoassay reagent strip; a flexible element 30 is disposed between the detecting chamber and the specimen chamber, and the flexible element is a rubber flake, and the detecting chamber and the specimen chamber are separated by the sheet-like rubber flake so that they are not in liquid communication, i.e., there is no liquid exchange between them (such as in FIG. 10A). A cross-shaped cutting slot 33 is cut on the rubber flake with a sharp knife in advance. When there is no external force or the external force is not sufficient, the cutting slot 33 is still in the first status of self-closed or sealed (such as in FIG. 10B) when a certain amount of liquid specimen 66 is collected in the specimen chamber. At this time, the liquid specimen 66 in the specimen chamber cannot flow into the detecting chamber via the cross-shaped cutting slot. When the rubber flake receives external forces, for example, rubber flake 30 is pressed by a rod like subject 14, the rubber flake 30 undergoes elastic deformation, and the self-closed cutting slot 33 is opened and is in the second status; at this time, part of the liquid specimen 67 in the specimen chamber flows into the detecting chamber via the opened cutting slot and has contact with the detecting element 700, and whether the liquid specimen contains the particular analytes (such as in FIGS. 10C and 10D) can be detected through the detecting element. When part of the liquid specimen enters the detecting chamber, it allows the external force forcing the rubber flake 30 to disappear, for example, the rod like subject 14 is no longer in contact with the rubber flake. At this time, the cutting slot 33 that is originally opened goes back to the self-closed or self-sealed status because of the flexibility, and the liquid that originally flows to the detecting chamber is blocked (such as in FIG. 10E). The rubber flake of the flexible element may have a thickness of 0-30 millimeters, preferably 1-15 millimeters, and even more preferably 2-5 millimeters; for example, it can be such as 1 millimeter, 2 millimeters, 3 millimeters, 5 millimeters, or 10 millimeters. The cutting slot may have an area of 1-10 cm$^2$ or 2-5 cm$^2$. What material to use and how to choose suitable thickness or size of the cutting slot can be determined according to requirements, which can be accomplished by a person skilled in the art according to teachings of the present invention combining the prior art. In examples in the present application, a small hole can be opened on the detecting chamber and the detecting chamber is in communication with the environmental pressure so that the liquid specimen can flow into the detecting chamber through the cutting slot 33 more naturally and fluently from the specimen chamber. In addition, the specimen chamber can also be in communication with the environmental pressure. When the cutting slot 33 is opened, part of the liquid specimen may be forced to flow into the detecting chamber via the opened cutting slot with the aid of the pressure of the liquid specimen itself or the pressure difference between the liquid specimen and the detecting chamber.

FIGS. 11A-11D is a detection device in another specific example of the present invention. The detection device comprises a specimen chamber 61, and the opening at one end of the specimen chamber is for receiving liquid specimen such as urine, with another end closed. A hole (not shown) is opened at the closed end and is sealed with a rubber sheet 13 having the same size as that of the hole. Further, the detection device also comprises a chamber 40, and part of the chamber 401 is at the closed end of the specimen chamber and is beneath the rubber sheet 13, and another part of the chamber 402 comprises a detecting element 700. A small hole 133 is opened on the rubber sheet 13 in advance, and when the rubber sheet is in natural status or only the specimen chamber contains the liquid specimen, the small hole 133 is the first status, i.e., the self-closed or sealed status, and is in the "—" liked shape; at this time, the liquid specimen in the specimen chamber cannot get into the detecting chamber 40 via the small hole, as shown in FIG. 11B. When the opening of the specimen chamber 61 is sealed by a cover 80 having a push rod 24, the push rod moves from the top to bottom to have contact with the rubber sheet and presses the opening or other places of the rubber sheet 13 gradually when the lid is rotating down. Because of the self flexibility, the small hole 133 that is self-sealed originally now gradually opens and is in the second status, and the liquid in the liquid specimen chamber enters the detecting chamber via the small hole 133 and is in contact with the detecting element, as shown in FIGS. 11C and 10D.

Alternatively, the self-closed rubber sheet can be pressed to open rather than be opened by the push rod directly. The specimen chamber can be allowed to be sealed by the cover, and the pressure on the surface of the liquid in chamber 61 can be increased in relative to the atmosphere pressure, consequently, the increased pressure can force the small hole that is self-closed to open indirectly, and the liquid specimen to enter into the detecting chamber. In addition, the pressure on the surface of the liquid in the specimen chamber can be adjusted to the same as the atmosphere pressure again, and at this time, the opened small hole goes back to the self-closed or sealed status due to disappearing of the external force, whereby blocking the liquid specimen from flowing into the detecting chamber. The method of adjusting the pressure on the surface of the liquid in the specimen chamber to the atmosphere pressure includes: opening a small hole on the cover, and sealing the small hole by a plastic soft cork, and allowing the pressure in the specimen chamber to increase; when the pressure needs to be reduced, taking out the cork and allowing the specimen chamber to connect with the atmosphere. The method and structure of increasing pressure are disclosed in the published Chinese Patent Application No. 200480033286.8. All the examples therein are cited and enclosed herein as specific examples of the present invention.

Figure 2:
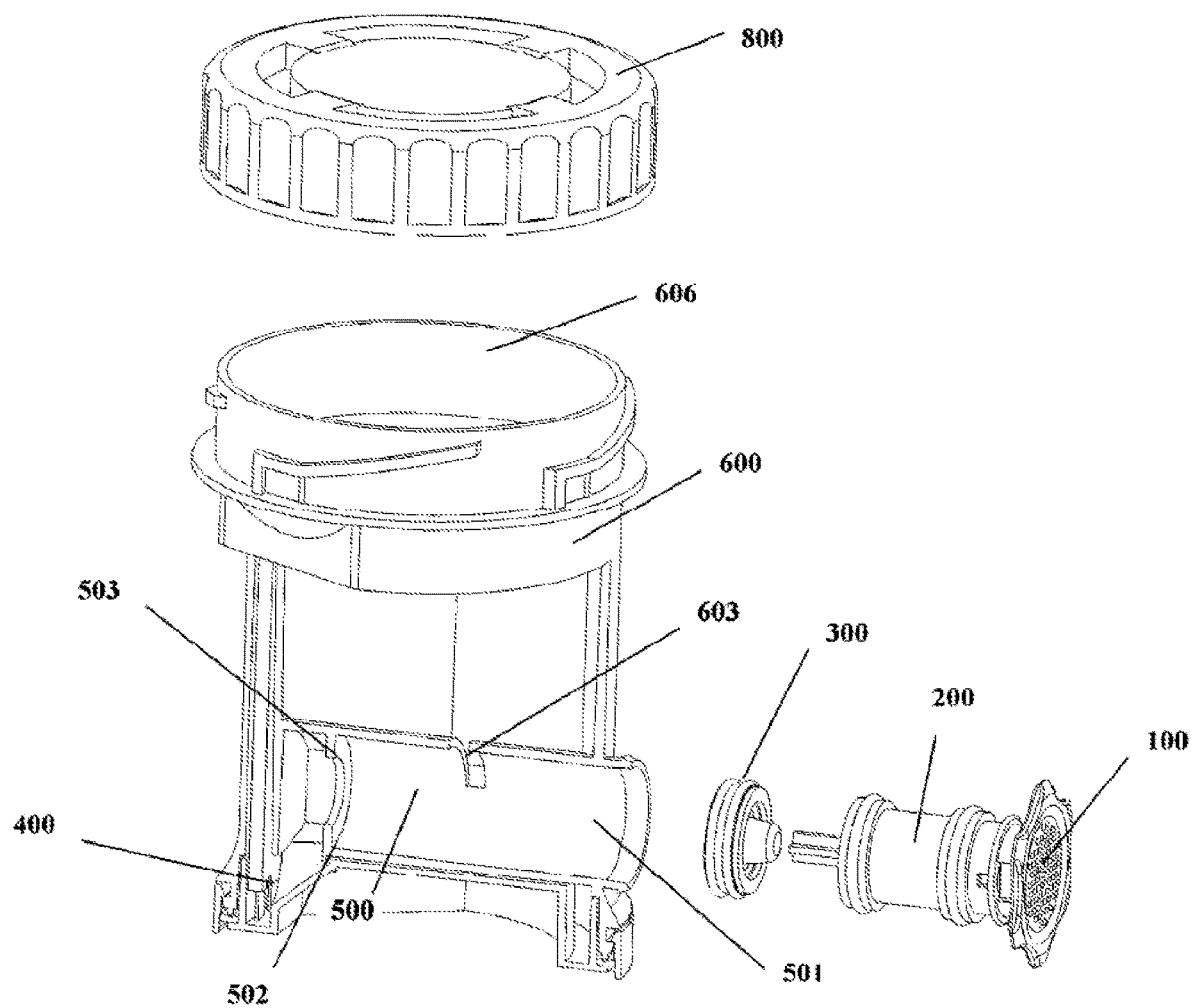
FIG. 2 is a schematic diagram of the exploded structure of the device shown in FIG. 1.

FIGS. 1-7 illustrate the detection device and the method of using it in another specific example of the present invention. As shown in FIG. 1 and FIG. 2, the device comprises a specimen chamber 601, a detecting chamber 400, and a nipple-shaped flexible element 300. The specimen chamber 601 and the nipple element 300 are in the cup body 600, an opening 606 of which collects the liquid specimen to the specimen chamber 601, the bottom of which comprises a channel 603 that is in communication with a transferring chamber 500, and the specimen chamber 601 is in communication with the transferring chamber 500 via a channel 603, and the bottom of the collecting chamber 601 and the transferring chamber share a wall, and the channel 603 is on this wall. Two ends of the transferring chamber 500 are open, and on the opening 502 close to the detecting chamber 400 a nipple-shaped flexible element 300 is disposed, and on the opening far from the detecting chamber and near the channel 603 a piston 200 is comprised, and the piston is within the empty chamber of the transferring chamber, and the piston can move left and right in the transferring chamber 500. The piston 200 comprises flexible sealed elements 201, 202, and the sealed elements are for sealing the inside wall of the transferring chamber and the outside wall 203 of the piston. Therefore, a chamber 900 is defined between the nipple element 300 and the piston 200 that receives the liquid specimen in the specimen chamber via the channel 603.

Referring to FIGS. 6A-6B and 7A-7B, the nipple-shaped flexible element 300 comprises a convex portion and a seat base 301, and the convex portion comprises the side wall 304 and the top 302, and a through hole 303 is opened on the side wall 304; the side wall 304 and the top 302 enclose a nipple chamber 305. The base part 301 comprises a groove 306, which cooperate with the annular convex edge 503 of the transferring chamber to allow the seat base of the nipple element to be installed and sealed on the opening 502 at one end of the transferring chamber. When the nipple-shaped flexible element 300 is in the first status, the convex portion of the nipple, i.e., the chamber of the nipple, is towards right, and the hole 303 is self-sealed at the time due to the self flexibility of the nipple chamber 305. When the nipple chamber 305 is forced to turn over and the top 302 is on left of the seat base part 301, the through hole 303 that is in the sealed or closed status is forced to opened. In one specific example, a push rod 204 is integrated with the piston as one piece and is right on the top of the top 302 of the nipple-shaped flexible element 300, and the push rod 204 moves from right to left when the piston moves from right to left in the transferring chamber. Therefore, the push rod can force the top 302 moves from the right of the seat base part 301 to the left of the seat base part 301. Certainly, in other alternative embodiments, the through hole can also be opened at other places rather than on the side wall, such as on other positions of the top or the side wall.

By reference to the figures, the operating mechanism of the detection device is further described in details as follows.

Figure 3A:
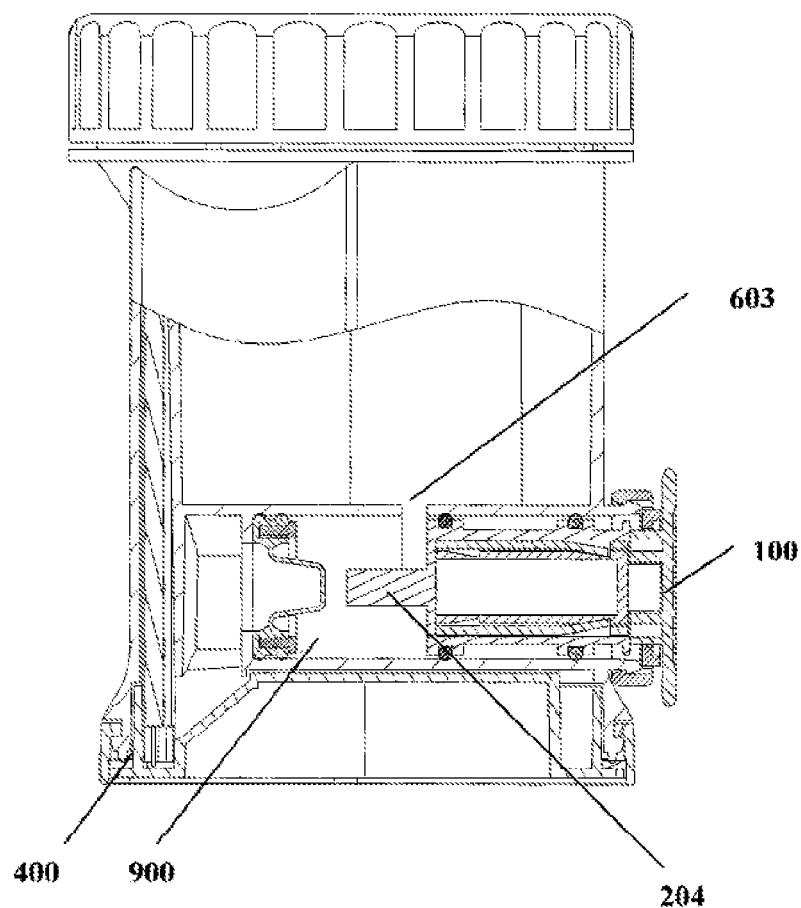
FIG. 3A is a vertical sectional schematic diagram of the structure of the device shown in FIG. 1, wherein the through hole is in the first status and the piston push rod is in the first position.
Figure 3B:
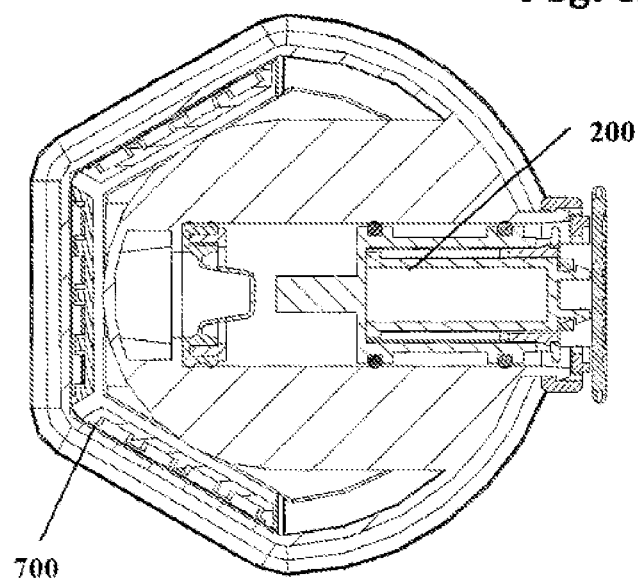
FIG. 3B is a cross sectional schematic diagram of the structure of the device in FIG. 3A, wherein the through hole is in the first status and the piston push rod is in the first position.

When in the first status, referring to FIGS. 1-3, the top 302 of the nipple flexible element is towards right, and the piston that is in its first position is within the transferring chamber (or called the piston chamber) 500 and defines a chamber 900 together with the nipple-liked flexible element, and the side wall of the chamber 900 comprises a channel 603, the sealing element of the piston, such as sealing rings 201 and 202, seals the outside wall of the piston with the inside wall of the transferring chamber 500. Moreover, the piston does not seal the channel 603, as shown in FIGS. 1 and 3A-3B. At this time, when the liquid specimen is collected with the device, if the specimen chamber is full of the liquid specimen, part of the liquid specimen flows into the chamber 900 via the channel 603. However, as the through hole 303 on the nipple-liked flexible element 300 is in the self-closed or sealed first status, the liquid specimen cannot flow into the detecting chamber 400 via the through hole on the nipple-liked flexible element. Although the liquid specimen in the liquid specimen chamber generates some stress or pressure on the through hole 303 on the nipple flexible element 300, as well as on the top 302 of the nipple, the stress or pressure is not sufficient to force the self-closed or sealed through hole to open. In addition, the piston 200 seals another end of the transferring chamber 500, and therefore, the volume of the liquid specimen inside the chamber 900 is fixed. Of course, the volume of the chamber can be freely chosen, such as 1-5 milliliters, or 2-10 milliliters, etc.

Figure 4A:
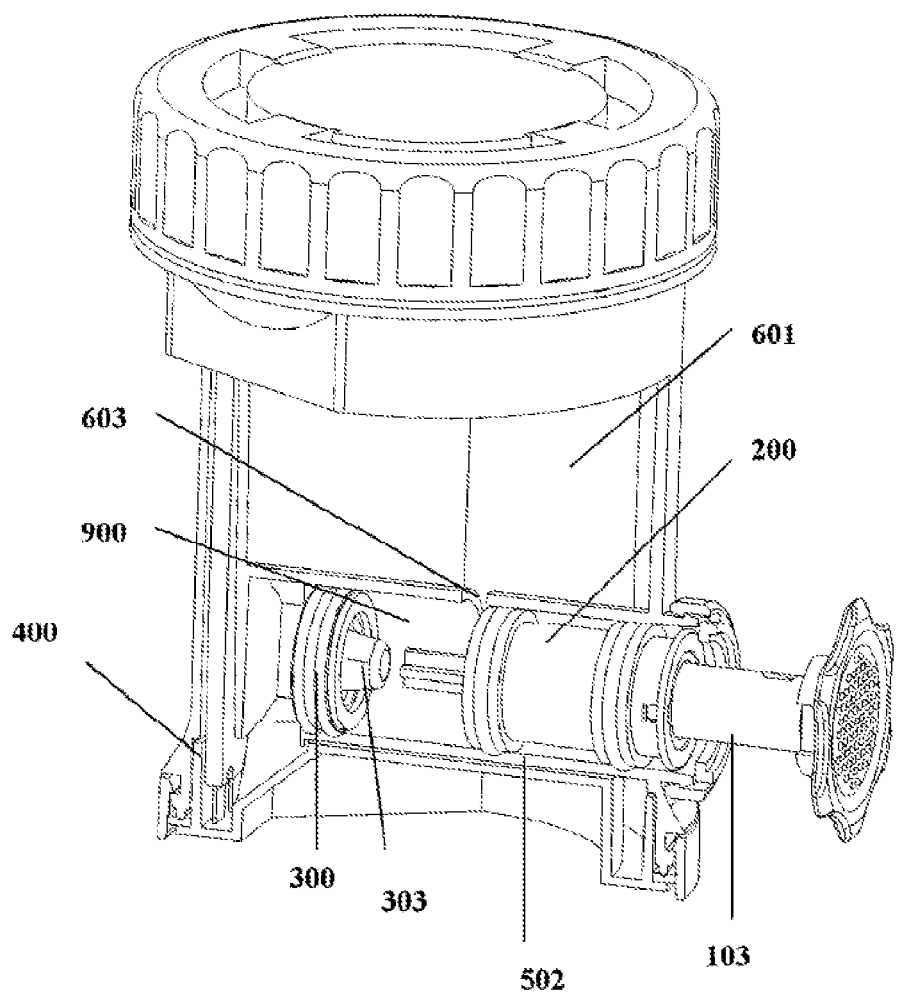
FIG. 4A is a stereostructural schematic diagram of the device shown in FIG. 3A, wherein the through hole is the first status and the piston push rod is in the second position.
Figure 4B:
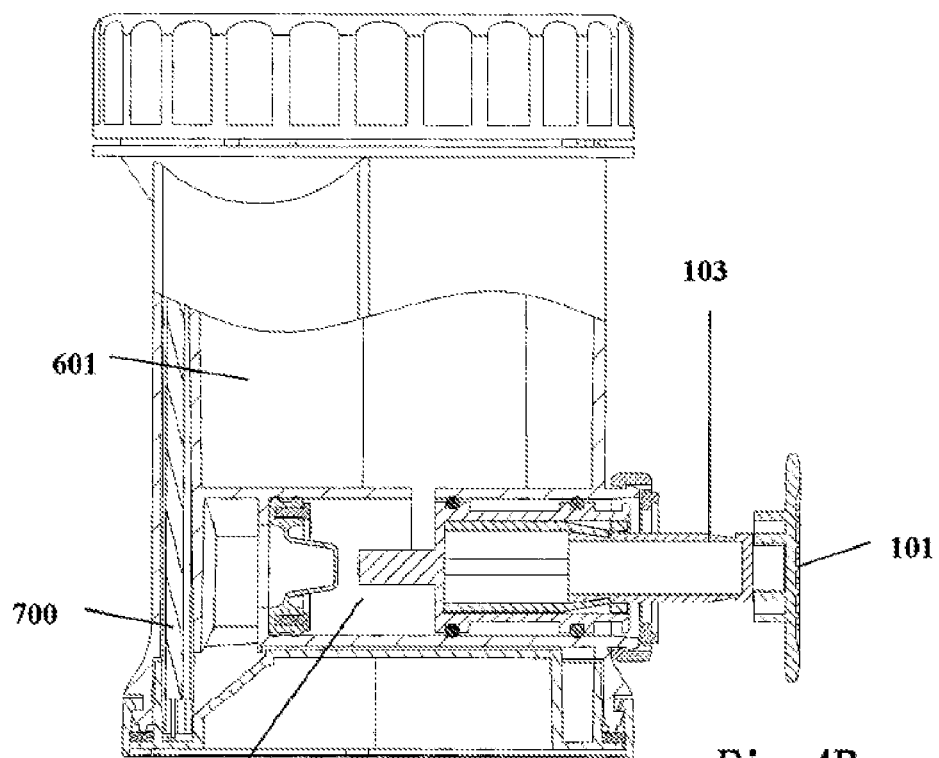
FIG. 4B is a partial vertical sectional schematic diagram of the structure of the device shown in FIG. 4A.
Figure 4C:
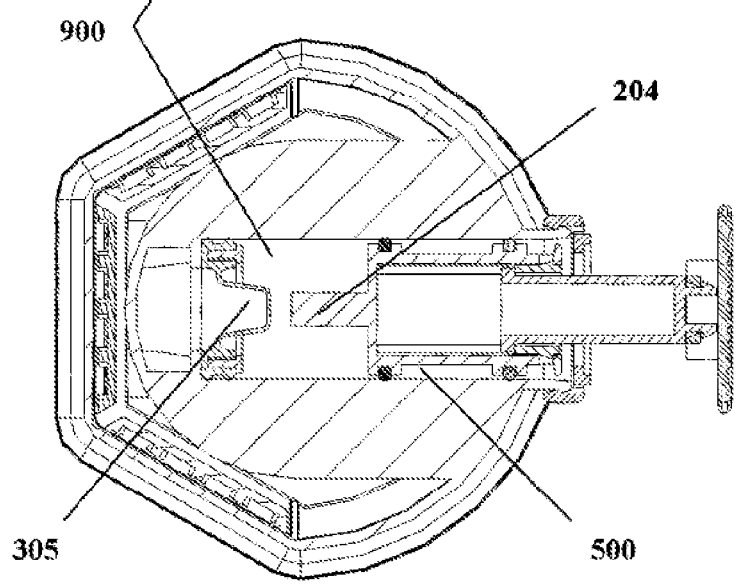
FIG. 4C is a cross sectional schematic diagram of the structure of the device shown in FIG. 4A.

When in use, referring to FIGS. 4A-4C, the piston push rod 100 that is in movable connection with the piston 200 is pulled away and the head 101 of the piston push rod is pushed, which moves the piston from a first position to a second position. During the moving process, the outside wall 203 of the piston seals the channel 603, and one end 205 of the top of the push rod 204 contacts with the top 302 of the nipple-liked flexible element 300. The chamber 900 is sealed completely at the time, which neither exchanges liquid with the specimen chamber nor with the detecting chamber.

Figure 5A:
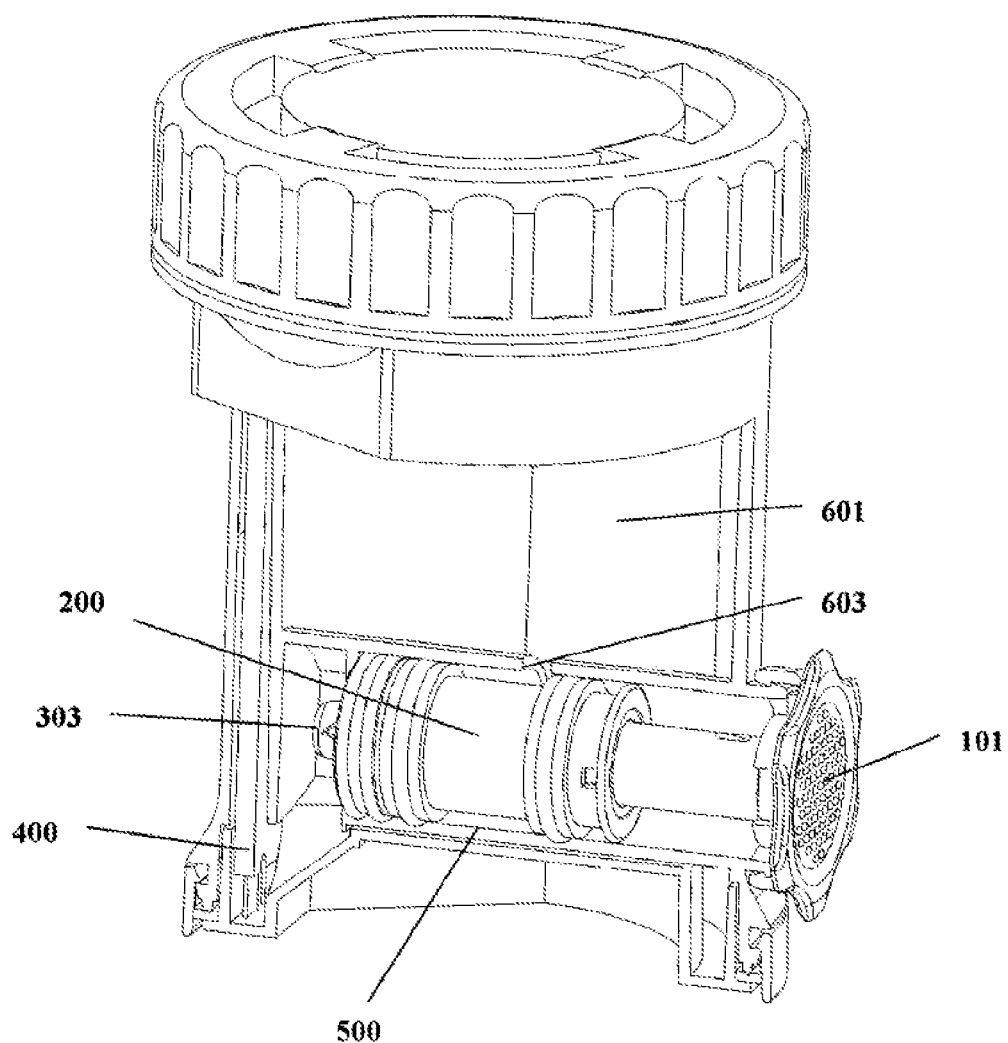
FIG. 5A is a stereostructural schematic diagram of a device described in a specific example of the present invention, wherein the through hole is in the second status and the piston is in the second position.
Figure 5B:
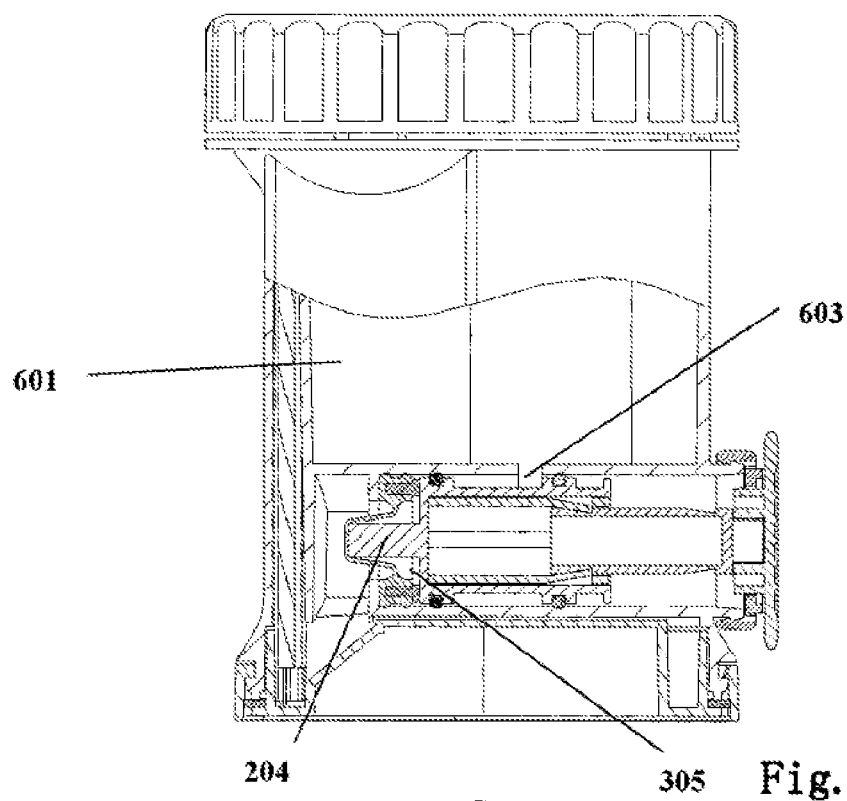
FIG. 5B is a partial vertical sectional schematic diagram of the structure of the device shown in FIG. 5A.
Figure 5C:
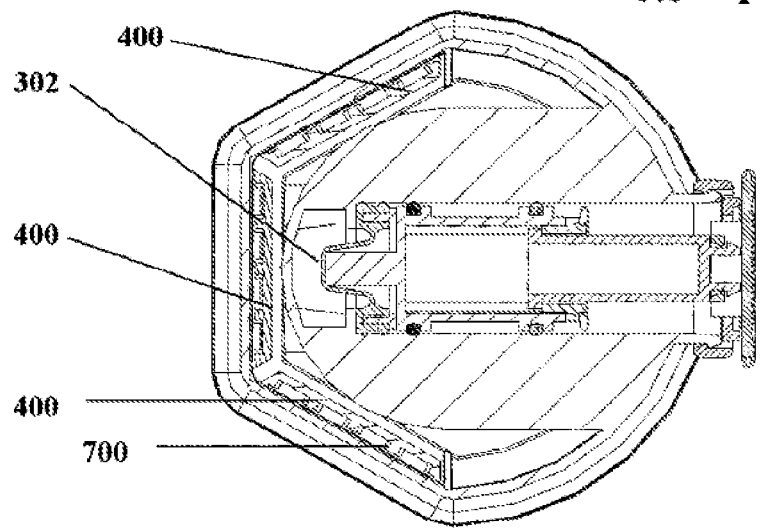
FIG. 5C is a cross sectional schematic diagram of the structure of the device shown in FIG. 5A.
Figure 6A:
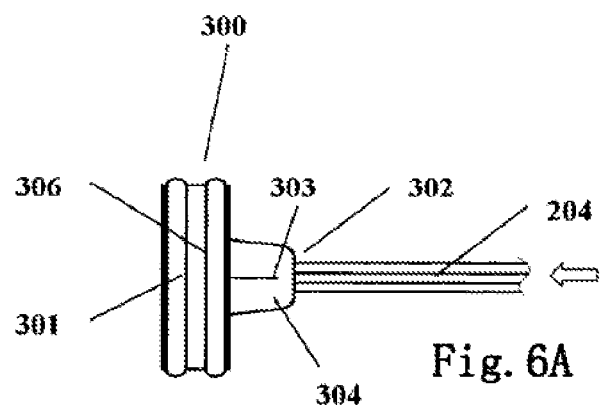
FIG. 6A is a stereostructural schematic diagram when the nipple element is in the first status.
Figure 6B:
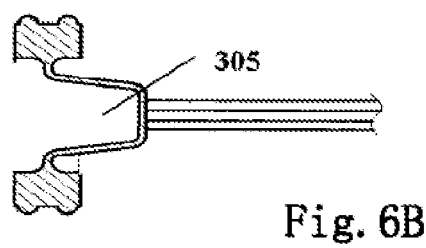
FIG. 6B is a sectional schematic diagram of the structure of the nipple element in the first status.
Figure 7A:
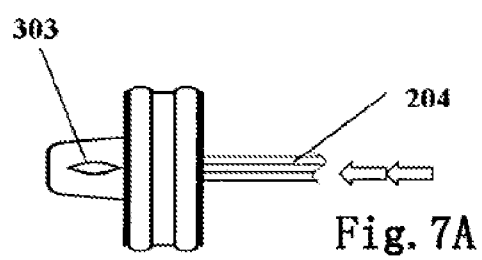
FIG. 7A is a stereostructural schematic diagram of the nipple element in a second status.
Figure 7B:
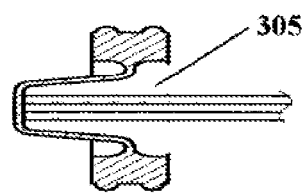
FIG. 7B is a sectional schematic diagram of the structure of the nipple element in the second status.

Referring to FIGS. 5A-5C, when the piston further moves to a second position, the push rod 204 that is integrated with the piston as one piece forces the chamber 305 of the nipple element to turn over, from towards right to towards left, and the top 304 of the nipple element 300 is changed from within the chamber 900 to within the detecting chamber 400. Since the side wall of the nipple element 300 is turned inside out, the through hole 303 that is on the side wall 304 of the nipple element 300 is now in its opened second status, and moving of the piston forces the liquid specimen in the chamber 900 enters the detecting chamber 400 via the through hole 303 to have contact with the detecting element 700, and whether the liquid specimen contains the analyte can then be detected through the detecting element. At this time, the chamber 900 is in liquid communication with the detecting chamber, but is not in liquid communication with the specimen chamber 601.

In one embodiment, the piston 200 and the piston push rod 100 are a moveable connection. When it needs to push the piston to move in the transferring chamber 500 through the piston push rod 100, the piston push rod 100 is pulled out from the piston chamber 210, and then fixed with the piston 200 through a fixing mechanism so that there will be no relative movement between the piston 200 and the piston push rod 100; consequently, the piston and the piston push rod are integrated as one piece. When pushing the piston push rod 100, the piston and the piston push rod move together, driving the push rod 204 that is integrated with the piston as one piece to move together. Therefore, the nipple flexible element that is in the self-closed or sealed first status is changed to the second status by position moving of the push rod 204. See the following description for more details.

Figure 8A:
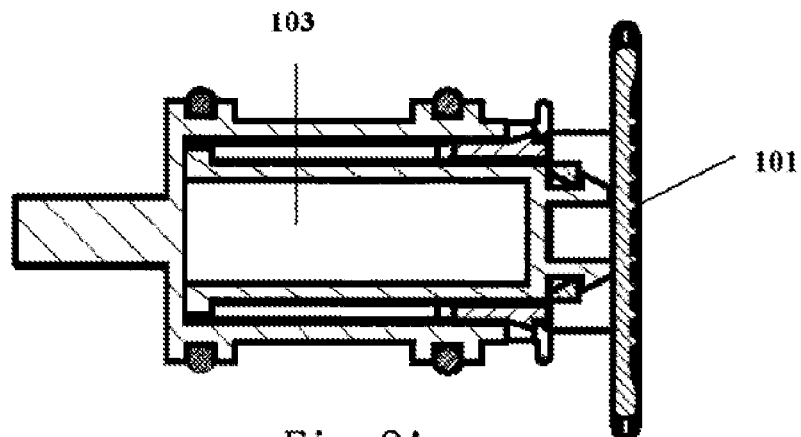
FIG. 8A is a sectional schematic diagram of the structure of the assembly of the piston and the piston push rod element shown in FIG. 8C.
Figure 8B:
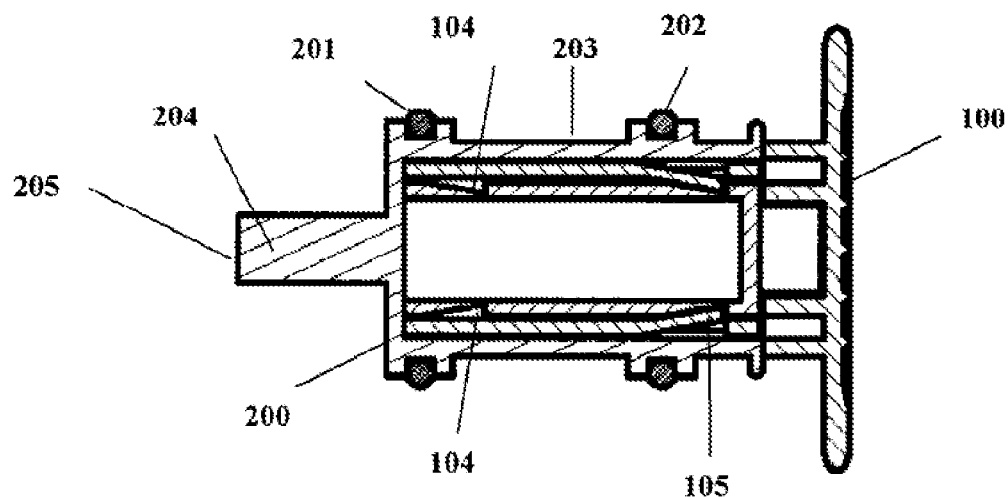
FIG. 8B is a schematic diagram of another section of the structure of the assembly of the piston and the piston push rod element shown in FIG. 8C.
Figure 8C:
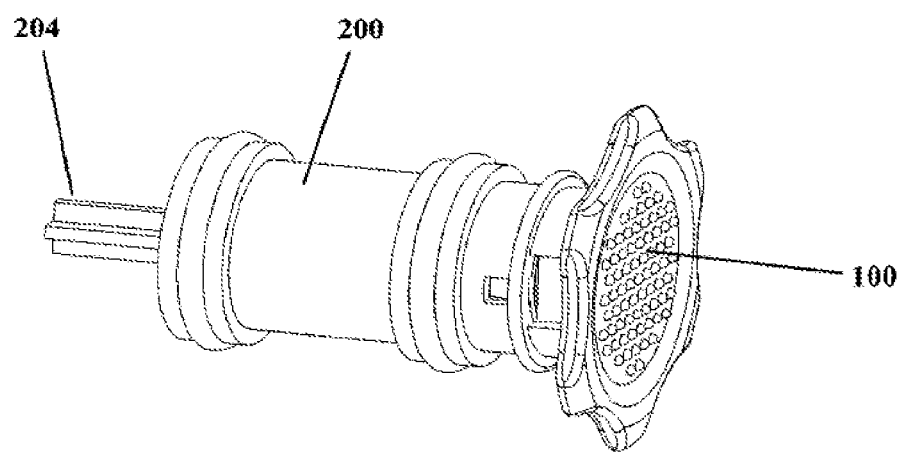
FIG. 8C is a stereostructural schematic diagram of the assembly of the piston and the piston push rod element (the piston rod is in the first position, the piston is in the first position).
Figure 9A:
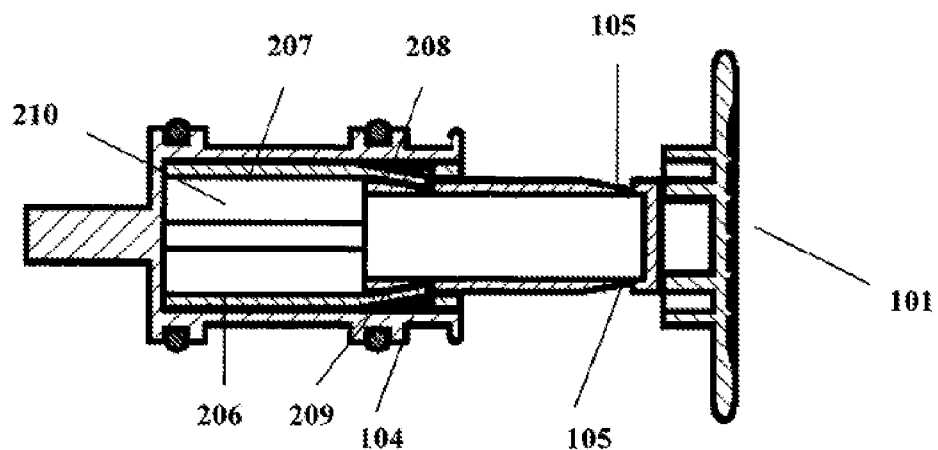
FIG. 9A is a sectional schematic diagram of the structure of the assembly of the piston and the piston push rod element shown in FIG. 9C.
Figure 9B:
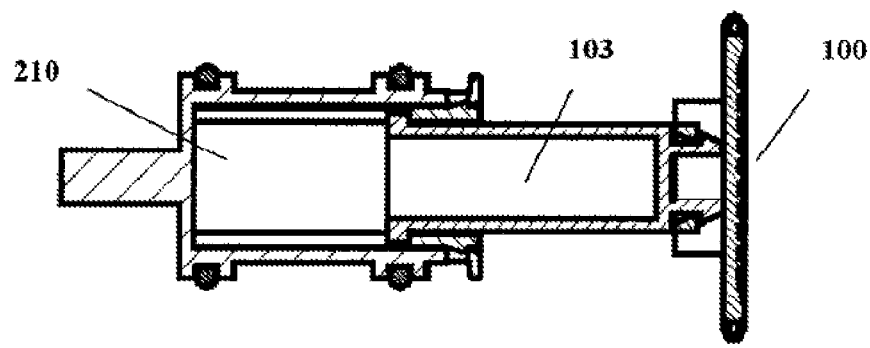
FIG. 9B is a schematic diagram of another section of the structure of the assembly of the piston and the piston push rod element shown in FIG. 9C.
Figure 9C:
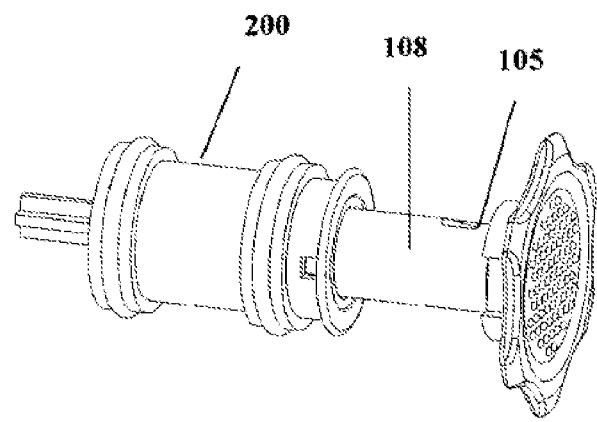
FIG. 9C is a stereostructural schematic diagram of the assembly of the piston and the piston push rod element (the piston rod is in the second position).

Referring to FIGS. 8A-8C and FIGS. 9A-92, the piston 200 is a cylinder, comprising a hollow chamber 210, and the outside wall 203 of the piston is disposed with two grooves for installing sealing elements 201, 202, and one end of the piston is sealed and has a rod-structured 204 protruding outward. The piston push rod 100 comprises a push rod body 103 and a head 101 connected with the body, and the outside wall 108 of the push rod body 103 comprises two pairs of clamping slots, the first pair of clamp slots 105, 105' and the second pair of clamp slots 104, 104'. The clamp slot has an upside down "L" shape. Two clamp strips 207, 206 are fixed on the inside wall of the piston chamber 210, respectively. One end of the clamp strips has downward bending end 208, 209, respectively. When the push rod body 103 is within the piston chamber 210, the bending ends of the two clamp strips 207, 206 are just fitting in the pair of slots 105, 105', and the pair of slots 104, 104' are vacant and in the status of not clamped by the clamp strips (FIG. 8B). When in operation, the pushing head 101 is pulled out toward right with hand, and the push rod body 103 is pulled out from the piston chamber 210 and a "click" sound can be heard, indicating that the ends 208, 209 of the clamp strips 207, 206 are moved to the second pair of slots 104, 104' from the first pair of slots 105, 105', respectively, and are clamping in the slots 104, 104' of the push rod body 103. Then the pushing head 101 is pushed toward left, because at this time the push rod body 103 is integrated with the piston 200 as one piece through the aforesaid clamp mechanism, and is no longer movable in relative to the piston, the piston is then pushed to its second position from its first position by the push rod body 103. Therefore, the rod 204 connected on the piston 200 moves from its first position to its second position, and the position moving of the push rod 204 changes the nipple-liked flexible element that is in the self-closed or sealed first status to the opened second status.

The push rod that is in a moveable connection with the piston can be used not only in the detection device of the present invention but also in other detection devices, as an independent structure unit.

The "specimen" in the present invention denotes any substances in which the presence and the concentration of the analyte need to be tested and/or analyzed, or one or more specimen in which the presence and the quantity of the analyte need to be tested and/or analyzed, or substances with which qualitative evaluation is needed. The specimen can be liquid specimen, such as liquid sample. Liquid samples comprise body fluids such as blood, serum, plasma, saliva, urine, tear, sperm and marrow; the liquid specimen can also be water samples such as seawater, lake water, river water, etc., or household water, municipal water uses or industrial water sources, runoff water or sewage water; the specimen can be food samples such as milk and wine. Mucus and semi-solid or solid specimen can be used to prepare samples such as liquid, eluate, suspension, or leaching solution. For example, samples of throat or genitalia can be soaked in liquid to prepare specimen. The specimen may comprise mixtures of liquid, solid and gas or any related mixtures, such as a cell suspension in a diluted fluid or a solution. The specimen comprises biomaterials such as cell, microorganism, organelle and biocomposite. The liquid specimen can be prepared and obtained from such as soil, dejecta, tissue, organ, biological body fluid or other non-liquid specimen in nature such as solid, semi-solid or highly viscous material. For example, these solid or semi-solid specimen can be mixed with suitable solutions such as diluted liquid. Specimen can be softened by soaking, frozen and unfrozen, or prepared to liquid samples by other extracting methods. The remaining particulate material can be removed with conventional methods such as filtering or depositing.

The analytes denoted in the present invention can be "drugs of abuse" (DOA) or other interested substances contained in the specimen. "Drugs of abuse" (DOA) refers to using drugs not for medical purposes (normally for paralysis of nerves). Abuse of the drugs will lead to body and spirit damages, generate dependency, addiction and/or death. Examples of drugs of abuse include cocaine, amphetamine (such as black beauty, white amphetamine tablets, dexamphetamine, dextro-amphetamine, Beans); methamphetamine (crank, methamphetamine, crystal, speed); barbiturate (such as Valium, Roche pharmaceuticals, Nutley, N.J.); ataractic (drugs for assisting sleeping); lysergic acid diethylamide (LSD); depressor (downers, goofballs, barbs, blue devils, yellow jackets, methaqualone); tricyclic antidepressants (TCA, i.e., imipramine, amitriptyline and doxepin); phencyclidine (PCP), tetrahydrocannabinol (THC, pot, dope, hash, weed, etc.); opiates (i.e., morphia, opium, codeine, heroin, oxycodone); antianxiety drug and sedative-hypnotic drugs, antianxiety drug is mainly for reducing anxiety, tension, fears and stabilizing emotion as well as sedative-hypnotic, including benzodiazepines (BZs), non-typical BZs, fused-dinitrogen-NB23Cs, benzazepins, ligands of BZ acceptors, ring-opening BZs, diphenylmethane derivatives, piperazinecarboxylates, piperidinecarboxylates, quinazoline ketones, thiazine and thiazole derivatives, other heterocyclics, sedative/anodyne of imidazole type, propylene glycol derivatives—carbamates, aliphatic compounds, and anthracene derivatives. The device can also be used to detect drugs which are for medical purposes but are easily overdosed such as tricyclic antidepressants (imipramine or analogs) and acetaminophen. These drugs will be decomposed to different small molecules after absorbed by human body, and the small molecules are present in body fluids such as blood, urine, saliva, and perspiration.

Detecting Element 700

The device of the present invention can use various test strips as its detecting element, depending on the analytes to be detected and the purpose of the detection. There are mainly two types of test strips: test strips for detecting and for preventing adulteration. The test strips for detecting include substances for detecting the components needed to be detected in the specimen. Test strips for preventing adulteration include substances for detecting the characteristic property of the specimen. Both types of strips comprise sample-adding area and detecting area.

Test Strips for Detecting: various test strips for detecting can be used in the present invention. The test strips for detecting comprise immunoassay detecting or chemical detecting of the concerned analytes in specimen. These analytes comprise: drugs of abuse or metabolites that indicate the health situation.

Take the "Drugs of Abuse" (DOA) described above as examples. The test strips of the present invention also can be used to detect drugs that are legal for medical purpose but are easily overdosed, which comprise: tricyclic antidepressants (imipramine and other analogs) and OTC products containing acetaminophen (such as drugs provided by McNeil-PPC Company located in Washington County, Pennsylvania, U.S.A. with the brand name of TYLENOL™). Such a detection may help emergency doctors to determine whether the patient overdoses certain drugs.

The metabolites in urine that can indicate the health situation comprise, but are not limited to, creatinine, bilirubin, nitrite, protein (nonspecific), hormone (such as human chorionic gonadotropin, luteal hormone, follicle stimulating hormone, etc.), blood, white blood cells, sugar, heavy metal or toxin, bacteria components (such as specific proteins and carbohydrates of special type of bacteria, such as *Escherichia coli* 0157: H7, *staphylococcus, salmonella, fusobacterium, Campylobacter, L. monocytogenes, vibrio,* or *Bacillus cereus*) and the physical properties such as the pH value and the specific gravity. Any other clinical chemical analytes presented in urine and suitable for rapid detecting method can be used in the present invention.

The test strips for detecting can be in various forms. Generally speaking, the test strips consist of water-absorbing materials. The water-absorbing materials comprise sample-adding area, test material area and detecting area. The specimen is added to the sample-adding area and migrates towards to the test material area due to the capillary effects. In the test material area, the specimen is dissolved and mixed with test materials needed for detecting the analytes (if present in the specimen). The specimen mixed with the test materials migrates to the detecting area subsequently. Additional test materials are fixed in the detecting area. These second group of test materials react with analytes (if present) or one of materials in the first group of test materials in the test material area. If the analyte exists in the specimen indeed, a signal will appear in the detecting are, and there will be no signal otherwise.

As a more specific example, the test strips for detecting revealed in the following U.S. patents or materials disclosed in patent applications can be used in the present invention: U.S. Pat. Nos. 5,252,496, 5,415,994, 5,559,041, 5,602,040, 5,656,503, 5,712,170, 5,877,028, 5,965,458, 6,046,058, 6,136,610, 6,140,136, 6,183,972, 6,187,268, 6,187,598, 6,194,221, 6,194,224, 6,221,678, 6,228,660, 6,241,689, 6,248,598, 6,271,046, 6,297,020, 6,316,205, 6,372,514, 6,338,969, 6,368,873, 6,372,516, 6,375,896, 6,375,897, 6,391,652, 6,403,383, 6,418,606, 6,429,026, 6,464,939, 6,468,474, 6,485,982, 6,506,612, 6,514,769, 6,528,323, 6,548,019, 6,730,268, 2001/0004532, 2001/0021536, 2001/0023076, 2002/0001854, 2002/0004019, 2002/0031840, 2002/0031845, 2002/0052050, 2002/0085953, 2002/0137231, 2002/0173047, 2002/0132267, 2003/0129673, 2003/0207466, 2004/0018636 and 2004/0191760.

Test Strips for Preventing Adulteration: detecting strips for preventing adulteration are used for detecting characteristic property or material of specimen, such as temperature, specific gravity, pH value, as well as contamination of certain material, including contamination of oxidant, contamination of glutaconaldehyde, contamination of nitrite, contamination of ascorbic acid (vitamin C) and contamination of creatinine. For such a purpose, it is acceptable that the following test strips are used. The test strips combine reagents for detecting additional chemical substances or other reagents intending to frustrate detecting and testing intention. These test strips can be used in any forms, such as immunoassay or chemical reaction. In some examples, the test strips can include tests for creatinine and protein to detect whether the urine sample is diluted. The test strips for preventing adulteration also can detect vitamin B or other materials added to the urine sample to frustrate the detection. The materials comprise: glutaraldehyde, nitrite, chromate, vinegar, products with a "VISINE™" (provided by Pfizer Pharmaceuticals Limited located in the City of New York, N.Y., U.S.A.), sodium bicarbonate, products with a "DRANO™" (provided by S.C. Johnson Company located in Racine, Wis., U.S.A.), soft beverages, oxidants (such as bleaching reagent, hydrogen peroxide, pyridine, chlorinated chromate).

The above test strips for detecting characteristic property of liquid specimen materials can be also used in the present invention. These test strips comprise water-absorbing materials for passing the liquid specimen through the strips, filtering element in liquid communication with the water-absorbing materials, and test material pad in liquid communication with the filtering element and an optional transparent lid. The test material pad comprises test materials for generating signals that can be detected, and the signals are related to the characteristic property of the specimen and are observable through the transparent lid or transparent pan of the device (if used). The filtering element can be made by materials inhibiting reflux of liquid from the raw material pad to the water-absorbing material. The term "inhibiting reflux" refers to the flowing amount from the test material pad to the water-absorbing material in such a small amount that it cannot change the detecting results, or that the test materials transferred from the test material pad to the water-absorbing material or the adjacent test material pad is in such a small amount that it cannot be detected or cannot make the detecting results unclear. The test strips also can comprise water repellent material disposed between part of the filtering material and the water-absorbing material. The water repellent material is for inhibiting reflux of specimen from the test material pad to the water-absorbing material. The liquid specimen migrates and passes the whole test strip due to capillary action. The term "capillary action" refers to the physical effect generated through internal interaction between liquid and wall or interior of material well known to a person skilled in the art, and the physical effect can result in that the liquid passes through the material. The term "water-absorbing material" refers to materials that can attract or absorb fluid easily and the materials are suitable for the capillary action for transmitting fluid from a place of the material to another place. The "filtering element" may even promote diffusion of the specimen during flowing to the test material pad, therefore facilitating formation of uniform and detectable signals on the test material pad. The filtering element also inhibits reflux of specimen from the test material pad to the water-absorbing material, and, therefore, inhibits chemical substances of the test materials transmitting from a test material pad to another test material pad. The "water repellent material" refers to the material that does not allow the amount of fluid that could change the detecting results to pass through. The "water repellent material" is typically a barrier of fluid flow.

Other types of test strips for preventing adulteration can also be combined to the device of the present invention. For example, the test strips for preventing adulteration revealed in the following reference materials can be applied in the present application: 2002/0001845, 2002/0098512, 2002/0155028, 2003/0045003, U.S. Pat. Nos. 5,922,283, 6,248,598, 6,514,768, 6,537,823 and 6,548,019.

What is claimed is:

1. A method for detecting an analyte in a liquid sample, the method comprising:
    a) providing a detection device, the detection device comprising:
        a specimen chamber for collecting or storing the liquid sample;
        a detecting chamber for containing a detecting element;
        a liquid transferring chamber positioned between the specimen chamber and the detecting chamber; and
        a flexible nipple element positioned between the detecting chamber and the liquid transferring chamber, the flexible nipple element having a shrinkable through hole for passing the liquid specimen between the liquid transferring chamber and the detecting chamber,
        wherein the flexible nipple element comprises a first and a second status, the through hole being self-sealed when in the first status, and the through hole being open when in the second status,
        wherein the flexible nipple element is reversibly movable between the first and second status such that the through hole is resealable,
        wherein when the flexible nipple element is in the first status, the specimen chamber is in liquid communication with the liquid transferring chamber, the detecting chamber is not in liquid communication with the liquid transferring chamber, and the through hole is positioned inside the liquid transfer chamber and outside of the detecting chamber, and
        wherein when the flexible nipple element is in the second status, the detecting chamber is in liquid communication with the liquid transferring chamber via the through hole, the specimen chamber is not in liquid communication with the liquid transferring chamber, and the through hole is positioned inside the detecting chamber and outside of the liquid transferring chamber;

b) shifting the flexible nipple element from the first status to the second status, thereby allowing the liquid specimen to flow into the detecting chamber from the collecting chamber via the through hole.

2. The method of claim 1, further comprising applying a rod to the flexible nipple element, wherein when the rod is moved from a first position to a second position, the flexible nipple element is changed to the second status from the first status.

3. The method of claim 2, further comprising, allowing the flexible nipple element to change from the second status to the first status.

* * * * *